(12) United States Patent
Arnhold

(10) Patent No.: US 8,298,241 B2
(45) Date of Patent: Oct. 30, 2012

(54) UNIVERSAL EXTRACTOR FOR TOTAL ENDOPROSTHESES (TEP) OF THE KNEE JOINT

(75) Inventor: Michael Arnhold, Eisenberg (DE)

(73) Assignee: Christian Arnhold, Eisenberg (DE)

( * ) Notice: Subject to any disclaimer, the term of this patent is extended or adjusted under 35 U.S.C. 154(b) by 361 days.

(21) Appl. No.: 12/310,806

(22) PCT Filed: Aug. 13, 2007

(86) PCT No.: PCT/DE2007/001460
§ 371 (c)(1),
(2), (4) Date: Mar. 6, 2009

(87) PCT Pub. No.: WO2008/028451
PCT Pub. Date: Mar. 13, 2008

(65) Prior Publication Data
US 2009/0240254 A1 Sep. 24, 2009

(30) Foreign Application Priority Data
Sep. 6, 2006 (DE) .......................... 10 2006 042 141

(51) Int. Cl.
*A61B 17/88* (2006.01)
*A61F 2/46* (2006.01)

(52) U.S. Cl. .......................................... 606/99; 606/207

(58) Field of Classification Search .................. 606/99, 606/151, 205–209; 29/268; 81/415, 427; 269/3, 6, 95
See application file for complete search history.

(56) References Cited

U.S. PATENT DOCUMENTS

| | | | |
|---|---|---|---|
| 1,047,046 A * | 12/1912 | Gronkowski | 81/163 |
| 4,601,289 A | 7/1986 | Chiarizzio | |
| 5,732,992 A | 3/1998 | Mauldin | |
| 5,735,857 A * | 4/1998 | Lane | 606/99 |
| 5,933,935 A * | 8/1999 | Alcorn | 29/229 |
| 6,582,451 B1 * | 6/2003 | Marucci et al. | 606/207 |

FOREIGN PATENT DOCUMENTS

| | | |
|---|---|---|
| DE | 100 13 331 | 9/2001 |
| WO | WO-93/25164 | 12/1993 |
| WO | WO-2007/062103 | 5/2007 |

* cited by examiner

*Primary Examiner* — Kevin T Truong
*Assistant Examiner* — Larry E Waggle, Jr.
(74) *Attorney, Agent, or Firm* — Jordan and Hamburg LLP

(57) ABSTRACT

The invention relates to a universal extractor for total endoprostheses (TEP) of the knee joint. The object of the invention, namely to make available a universal extractor for artificial knee joints that avoids the disadvantages of the prior art, is achieved by the fact that the universal extractor comprises the following parts:
- a T-piece with an extraction plate and with a securing arm, the securing arm being fork-shaped and slotted at its distal end and supporting the extraction plate at its proximal end;
- a scissor mechanism with clamping jaws located at its free distal ends, said securing arm holding the scissor mechanism by means of a securing pin about which the scissor mechanism can move; and
- an eyebolt which is mounted on the proximal end of the scissor mechanism and has a knurled nut, the eyebolt being adjustable and connecting the ends of the scissor mechanism to each other, so as to permit fixing or release of the clamping jaws which have a shovel-shaped, U- to V-shaped geometry.

5 Claims, 1 Drawing Sheet

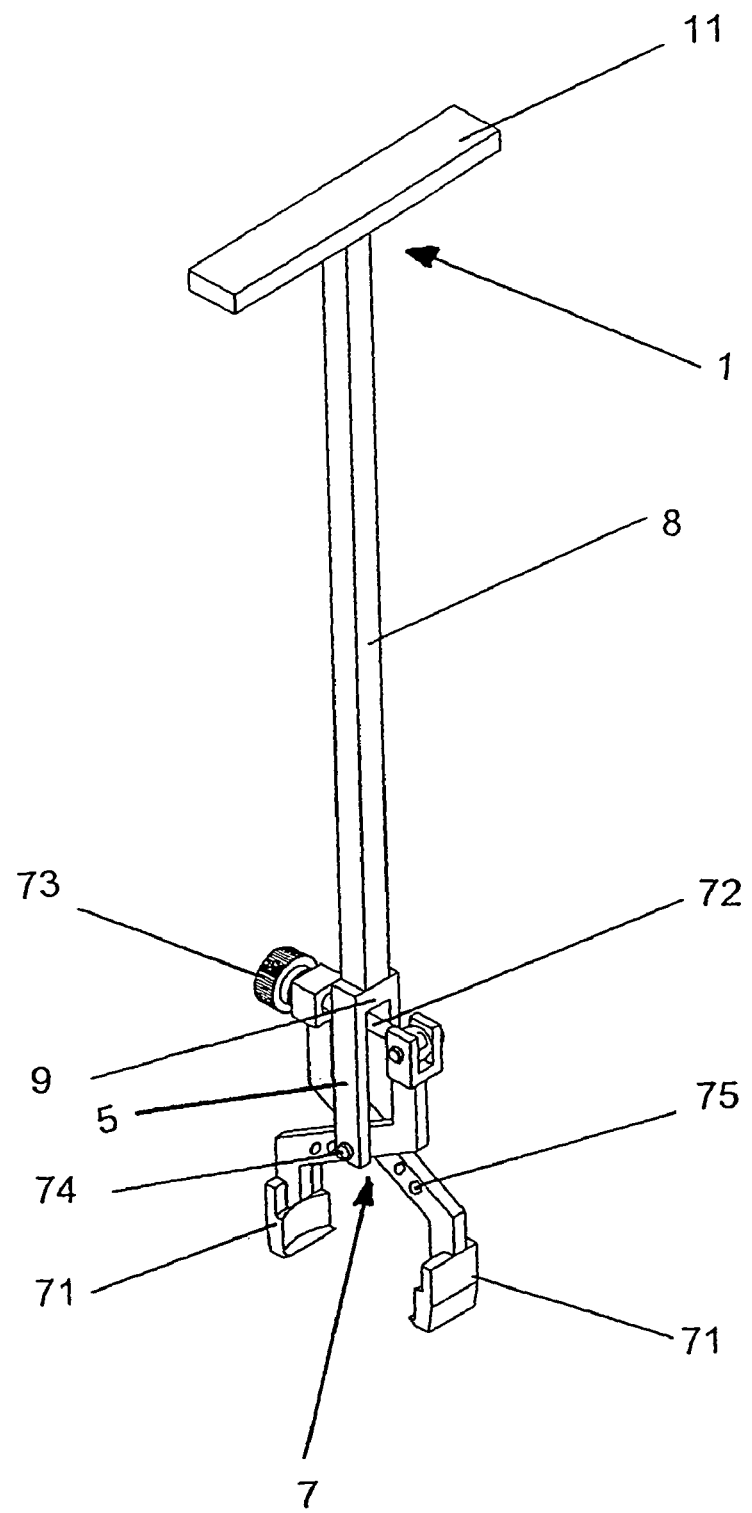

UNIVERSAL EXTRACTOR FOR TOTAL ENDOPROSTHESES (TEP) OF THE KNEE JOINT

BACKGROUND OF THE INVENTION

The invention relates to a universal extractor for total endoprostheses of the knee joint according to the species of the claims.

Only a few extractors and clamping devices are currently available; their mechanism is often not useful.

Thanks to the improvement made in the design of prostheses, the TEP of knee joints have reached almost the same importance as the ones of hip joints. But also the number of exchange operations is continuously increasing. The basic problems of such TEP can be compared with the ones combined with hip joint prostheses.

About 20 years ago the market of total endoprostheses was dominated by cemented, coupled prosthetic components provided with a shaft. If they loosened or infections developed, serious osseous defect situations were often caused. Usually, such prostheses could be removed without any problems. In case of persistent infections, an amputation was not uncommon.

In the period following, the uncoupled, mostly cement-free surface replacement prostheses that had several advantages took over the market.

If revision surgery is necessary, the removal of such prostheses is not unproblematic. But also here, in case of revision only a few technical solutions are available that allow the extraction of an implant without causing damage to the bones.

The few useful extractors for knee prosthetic components have the disadvantage that they do not allow a stable friction-fit anchoring at said components. Also the sledge hammers produce only an unsatisfactory power transmission during the explantation of the joint components.

In case of revision surgery, the rigid osseous integrated cement-free, more seldom also cemented, components must be "pre-loosened" by means of diverse tools. The object is to reduce the anchoring surface area of the prostheses and thus the shearing forces acting during the explantation. This is the only way to avoid secondary injuries for the osseous bed around the prosthesis or disadvantageous osteotomies and thus to facilitate the reimplantation of a revision prosthesis.

SUMMARY OF THE INVENTION

Therefore, it is the object of this invention to make available a universal extractor for knee prosthetic components that avoids the disadvantages of the prior art. For this purpose the following tasks, among others, are to be solved:
1. stable orthograde anchoring of the extractor at the prosthetic components of very different designs and sizes;
2. optimum development of the extraction force;
3. reusability of the extractor.

The inventive universal extractor comprises the following assemblies:
1. scissor mechanism with clamping jaws and eyebolt with knurled 20 nut,
2. securing bolts,
3. T-piece the axial arm of which is a slotted rod.

The stable anchoring mechanism of the universal extractor at the prosthetic component to be dislodged is based on two curved clamping jaws that are fixed at the distal ends of the scissor mechanism. Their shovel-shaped, approximately V-shaped to U-shaped geometry allows a stable self-centering fixation even at curved prosthetic edges. The reliable lock of the clamping jaws is ensured by an eyebolt with a knurled nut mounted on the proximal end of the scissor mechanism. This scissor mechanism is installed via a securing pin at the axial arm of the T-piece that is provided with an extraction plate. Thus, a stable coupling between the prosthetic component and the extraction plate is guaranteed and ensures the optimum development of the extraction force.

The clamping range of the scissor mechanism with its clamping jaws (i.e. the effective gripper distance of the clamping jaws) can be adjusted. This adjustment is achieved by three through holes that are provided in each arm of the scissor mechanism for holding the securing pins. As this arrangement allows to clamp various sizes and geometries of prosthetic components in a stable and orthograde manner the function of the inventive universal extractor is facilitated.

The stable orthograde anchoring of the inventive universal extractor is based on two self-centering clamping jaws that can be inserted into the border zone between the osseous bed and the prosthetic component. Independently of a straight or curved edge structure of a prosthetic component, the self-centering and thus the stable anchoring is obtained by the also curved structure of the inventive clamping jaws. But the radius of curvature of said jaws must be smaller than the one of the smallest prosthetic component.

After the stable fixation of the universal extractor at the prosthetic component, an optimum development of the extraction force by the extraction plate of the T-piece is reached by using a metal hammer. When the prosthesis is successfully removed, the fixation of the extractor and the prosthetic component can be eliminated without any problems. The continuously adjustable clamping and releasing of the scissor mechanism is an advantage of this invention.

The reusability of the universal extractor is ensured by the reversibility of its fixation and the possibility of its re-sterilization.

BRIEF DESCRIPTION OF THE DRAWING

In the following, the invention is explained in detail in a schematic drawing. It shows:

FIG. 1 an embodiment of the inventive universal extractor in a schematic spatial representation.

DETAILED DESCRIPTION OF THE INVENTION

The universal extractor 1 shown in FIG. 1 comprises a scissor mechanism 7 with clamping jaws 71 and a mounted eyebolt 72 provided with a knurled nut 73 comprising an actuating portion. Said scissor mechanism 7 is connected via a securing pin 74 with prongs 5 of the distal fork-shaped end 9 of the securing arm 8 of the T-piece, wherein end 9 serves as a prong 5 bridging member. The proximal end of the T-piece is formed by the extraction plate 11.

The inventive clamping jaws 71 are installed on the distal ends of the scissor mechanism 7. Said clamping jaws 71 have a shovel-shaped, V-shaped to U-shaped surface geometry (curved contact surface) that is oriented towards the prosthetic edge and ensures the stable, self-centering fixation of the extractor at the prosthetic component, which is to be removed, in its border range to the osseous bed. The fixation is realized by the eyebolt 72 with knurled nut 73 secured at the proximal end of the scissor mechanism 7. For prosthetic elements of different sizes the optimum clamping range of the clamping jaws 71 can be ensured, for example, by a securing pin 74 of the scissor mechanism 7. Said pin is supported in through holes 75 and for changing the clamping range it can be removed out of one through hole 75 at each arm of the scissor mechanism 7 and inserted into another. The through holes 75 in the arms of the scissor mechanism 7 must have the same orientation.

All elements presented in the description, the subsequent claims and the drawings can be decisive for the invention both as single elements and in any combination.

The invention claimed is:

1. Universal extractor for a knee prosthesis, comprising a T-shaped element having a vertical member and a horizontal member affixed to a first end of the vertical member, the horizontal member comprising an extraction plate for receiving an extraction force upon extraction of the prosthesis and the vertical member comprising a securing arm, a second end portion of the vertical member defining a terminal end portion of the vertical member from which a pair of fork-shaped prongs and a prong bridging member extend so as to define a slot between the prongs, the prongs being symmetrical about an axis that passes therebetween and that is parallel with a longitudinal axis of each of the prongs and extending along their longitudinal dimension into a plane that is orthogonal to a plane in which the extraction plate extends in a longitudinal direction of the extraction plate;

a scissor mechanism comprising two intersecting arms, an intersecting portion of the arms being received in the slot so that each of the arms is free from direct contact with either of the prongs at a point directly adjacent the bridging member and the prongs, a first pin pivotably connecting the arms to the second end portion of the vertical member and to the prongs, and a respective clamping jaw carried on a distal end of each of the arms, the clamping jaws each being shovel-shaped or substantially U- or V-shaped or of a shape intermediate a U and a V, the point of connection of the arms to the second end portion defining a locus of force transfer between the arms, prongs and extraction plate upon extraction of a prosthesis so as to optimize an extraction force exerted upon the extraction plate during extraction of the prosthesis; and an adjustment mechanism comprising an elongated member including an attached actuating portion, the adjustment mechanism adjustably connecting proximal ends of the arms so as to adjustably fix a distance between the proximal ends thereby to effect fixation and release of the jaws to and from a knee prosthesis, the arms being movable during a scissoring movement thereof through a plane that is orthogonal to the plane in which the longitudinal dimension of each of the prongs of the fork-shaped second end portion of the vertical member extends, and the actuating portion laying in a plane that is parallel to the plane through which scissoring movement of the arms occurs and orthogonal to the plane through which the longitudinal dimension of each of the prongs extends.

2. The universal extractor of claim 1, wherein the jaws are integral with the arms.

3. The universal extractor of claim 1, further comprising a respective aperture passing through each of the arms at the intersecting portion thereof to form a pair of axially aligned apertures through which the first pin passes.

4. The universal extractor of claim 3, further comprising at least one additional pair of apertures passing through the arms and through which the first pin is receivable, the apertures of each pair being spaced from other apertures in a length direction of the arms whereby changing the first pin from one of the pairs of the apertures to another of the pairs changes the location of the intersecting portions of the arms and also changes the clamping range of the jaws.

5. The universal extractor of claim 1, wherein the arms and the jaws are symmetrical about a plane through the T-shaped member thereby rendering the jaws self-centering.

* * * * *